(12) United States Patent
Sliwa et al.

(10) Patent No.: US 8,382,689 B2
(45) Date of Patent: Feb. 26, 2013

(54) DEVICE AND METHOD FOR HIGH INTENSITY FOCUSED ULTRASOUND ABLATION WITH ACOUSTIC LENS

(75) Inventors: John W. Sliwa, Los Altos, CA (US); Peter Goetz, Aptos, CA (US); Zhenyi Ma, San Jose, CA (US); Jennifer Teng, Santa Clara, CA (US); Stephen Morse, Menlo Park, CA (US); Frank Callaghan, Blaine, MN (US); Timothy E. Ciciarelli, San Jose, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1668 days.

(21) Appl. No.: 11/703,783

(22) Filed: Feb. 8, 2007

(65) Prior Publication Data

US 2008/0194965 A1    Aug. 14, 2008

(51) Int. Cl.
*A61H 1/00* (2006.01)
(52) U.S. Cl. .......................................................... 601/2
(58) Field of Classification Search ........................ 601/2
See application file for complete search history.

(56) References Cited

U.S. PATENT DOCUMENTS

| | | | |
|---|---|---|---|
| 3,958,559 A | 5/1976 | Glenn et al. | |
| 4,556,070 A | 12/1985 | Vaguine et al. | |
| 5,054,470 A | 10/1991 | Fry et al. | |
| 5,640,961 A * | 6/1997 | Verdonk | 600/459 |
| 5,664,456 A | 9/1997 | Eckert | |
| 5,680,863 A | 10/1997 | Hossack et al. | |
| 5,938,608 A | 8/1999 | Bieger et al. | |
| 6,004,269 A | 12/1999 | Crowley et al. | |
| 6,194,814 B1 | 2/2001 | Hanafy et al. | |
| 6,277,077 B1 | 8/2001 | Brisken et al. | |
| 6,500,133 B2 | 12/2002 | Martin et al. | |

(Continued)

FOREIGN PATENT DOCUMENTS

| DE | 10309605 | 9/2004 |
|---|---|---|
| EP | 0441997 | 8/1991 |

(Continued)

OTHER PUBLICATIONS

International Search Report and Written Opinion of the International Searching Authority for PCT/US/08/53260 filed Feb. 7, 2008, dated Aug. 8, 2008.

(Continued)

*Primary Examiner* — Unsu Jung
*Assistant Examiner* — Saurel J Selkin
(74) *Attorney, Agent, or Firm* — Wiley Rein LLP

(57) ABSTRACT

A high intensity focused ultrasound transducer includes an ultrasonic emitter having a surface that emits ultrasonic energy along a beam path, at least one low attenuation polymeric ultrasonic lens acoustically coupled to the surface in the beam path of the ultrasonic energy, such that the lens can direct the ultrasonic energy in at least one direction, and at least one stress mitigation feature, such as a kerf, a heat sink, or an acoustic matching layer, to mitigate thermal expansion mismatch stresses within the transducer. For manufacturing simplicity, the first surface is typically either flat or monotonically curvilinear. The lens may take a variety of shapes, including Fresnel features, and may focus, collimate, or defocus the ultrasonic energy. Any orientation and positioning of the at least one ultrasonic lens relative to the first ultrasonic emitter is contemplated. Manufacture is further simplified by molding, casting, or thermoforming the lens.

19 Claims, 7 Drawing Sheets

U.S. PATENT DOCUMENTS

| | | |
|---|---|---|
| 6,554,826 B1 | 4/2003 | Deardorff |
| 6,635,054 B2 | 10/2003 | Fjield et al. |
| 6,672,312 B2 | 1/2004 | Acker |
| 6,689,128 B2 | 2/2004 | Sliwa, Jr. et al. |
| 6,701,931 B2 | 3/2004 | Sliwa, Jr. et al. |
| 6,805,128 B1 | 10/2004 | Pless et al. |
| 6,805,129 B1 * | 10/2004 | Pless et al. ............. 128/898 |
| 6,858,026 B2 | 2/2005 | Sliwa, Jr. et al. |
| 7,070,565 B2 | 7/2006 | Vaezy et al. |
| 2002/0002371 A1 | 1/2002 | Acker et al. |
| 2002/0030423 A1 | 3/2002 | Fjield et al. |
| 2003/0060736 A1 * | 3/2003 | Martin et al. ............. 601/2 |
| 2003/0229331 A1 * | 12/2003 | Brisken et al. ............. 604/500 |
| 2004/0217675 A1 | 11/2004 | Desilets et al. |
| 2005/0096542 A1 * | 5/2005 | Weng et al. ............. 600/439 |
| 2006/0184071 A1 | 8/2006 | Klopotek |
| 2008/0097253 A1 * | 4/2008 | Pedersen et al. ............. 601/2 |

FOREIGN PATENT DOCUMENTS

| | | |
|---|---|---|
| WO | WO-89/07907 | 9/1989 |
| WO | WO-2006076269 | 7/2006 |

OTHER PUBLICATIONS

U.S. Appl. No. 11/646,526, filed Dec. 28, 2006, Crowe, et al.
U.S. Appl. No. 11/646,528, filed Dec. 28, 2006, Holzbaur, et al.
U.S. Appl. No. 11/642,923, filed Dec. 21, 2006, Podmore, et al.
U.S. Appl. No. 11/642,821, filed Dec. 21, 2006, Podmore, et al.
U.S. Appl. No. 11/647,295, filed Dec. 29, 2006, Crowe, et al.
U.S. Appl. No. 11/646,524, filed Dec. 28, 2006, Podmore, et al.
U.S. Appl. No. 11/703,784, filed Feb. 8, 2007, Sliwa, et al.
International Search Report for PCT/US08/53263 Filed Feb. 7, 2008 and Written Opinion dated Aug. 22, 2008.
"Supplementary European Search Report", EP Appln No. 08 729 243.9 Feb. 28, 2011.

* cited by examiner

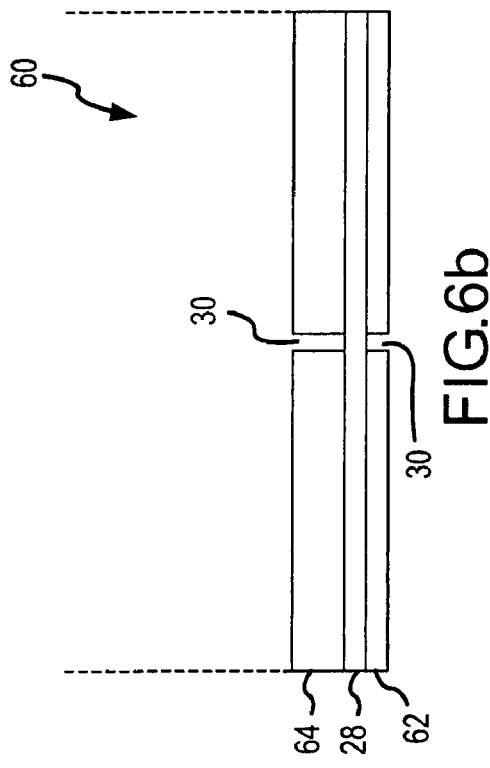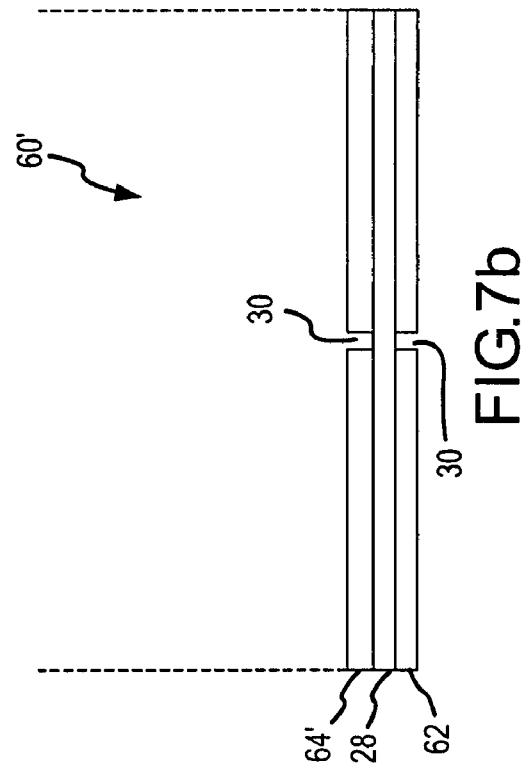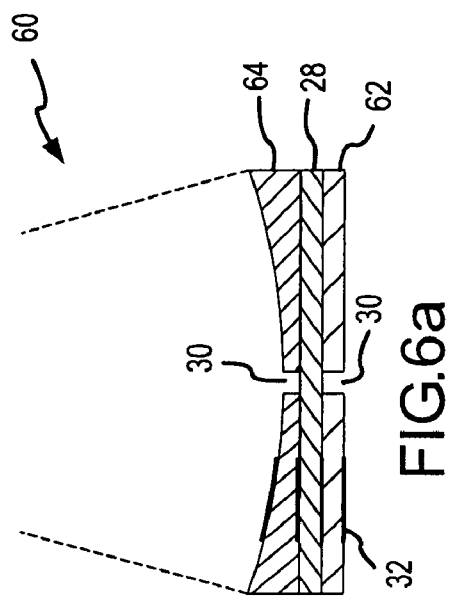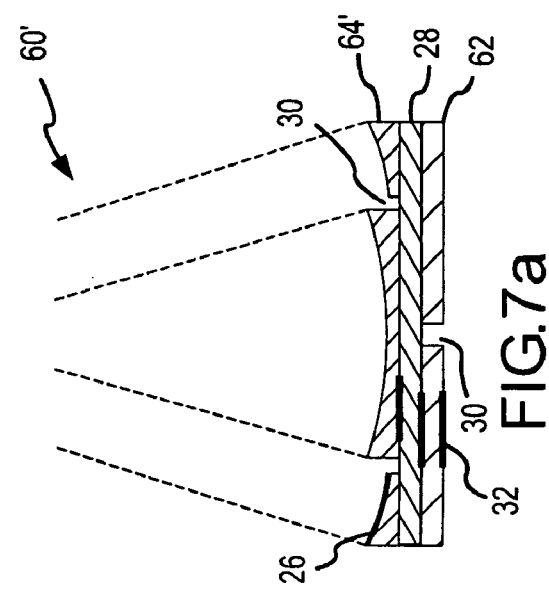

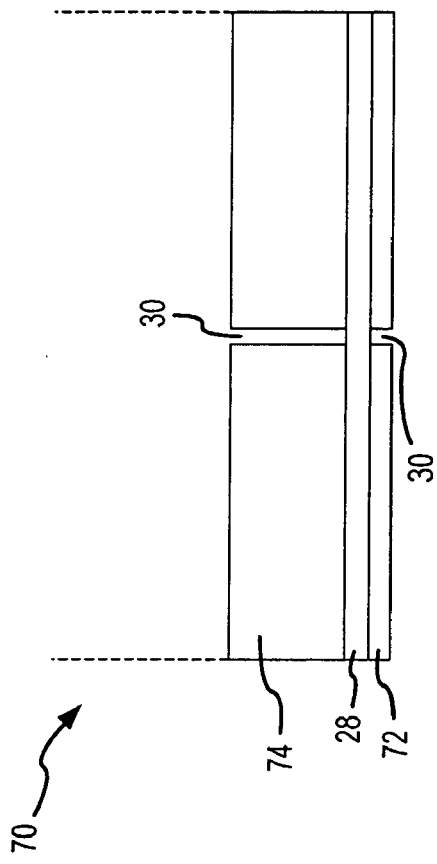
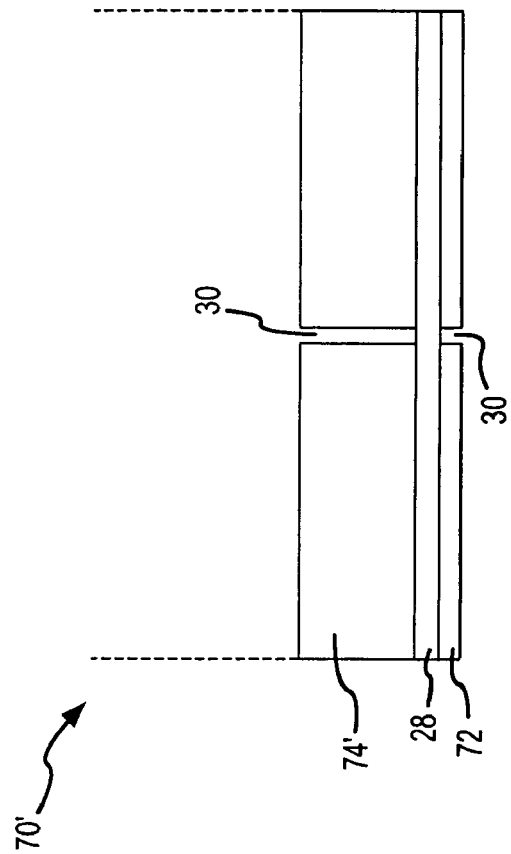
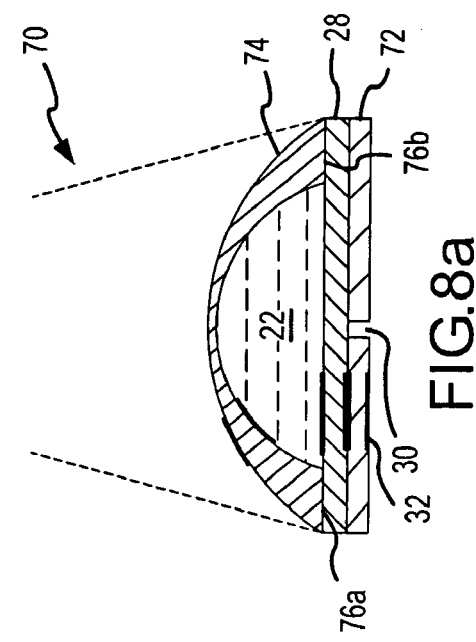
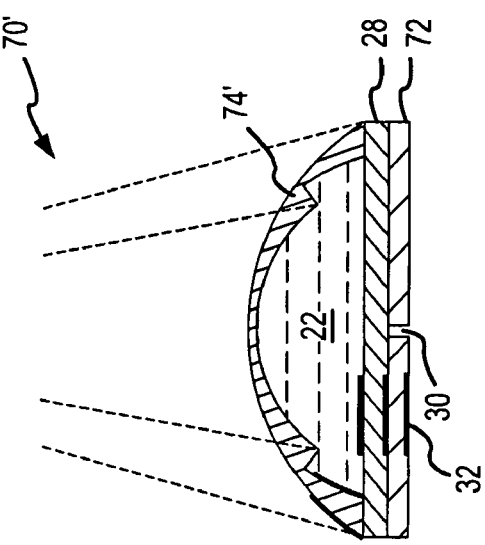

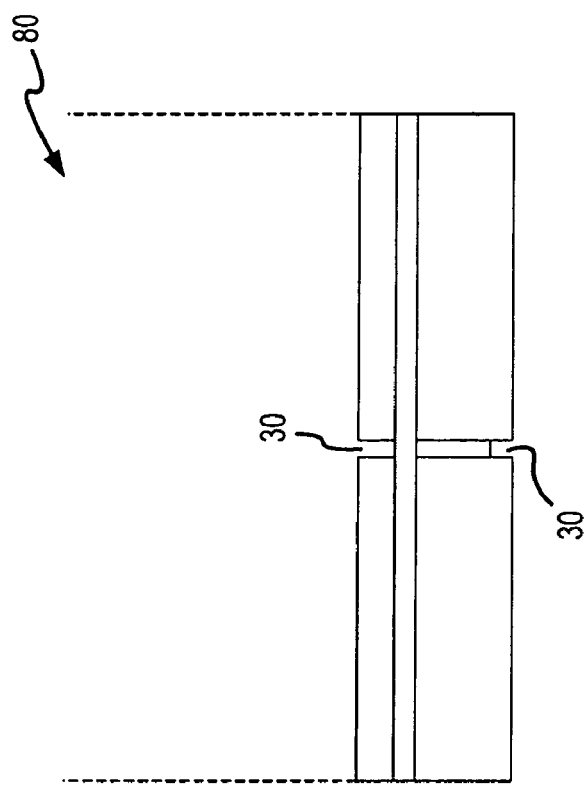
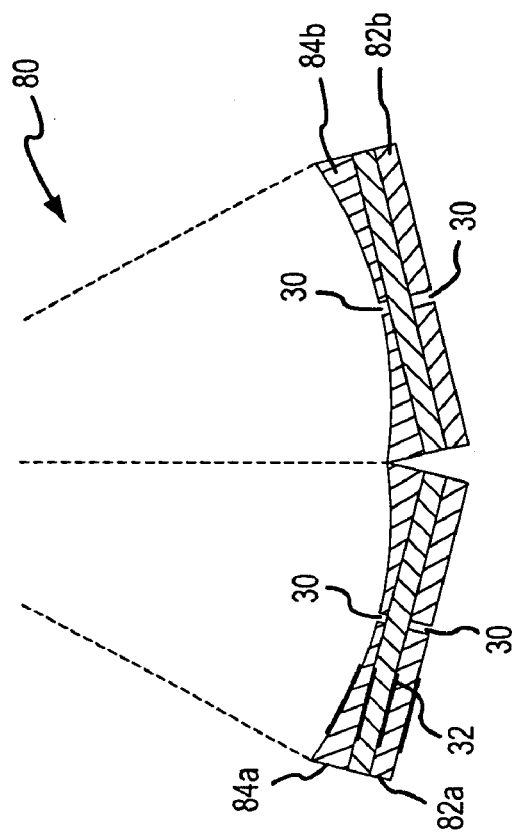

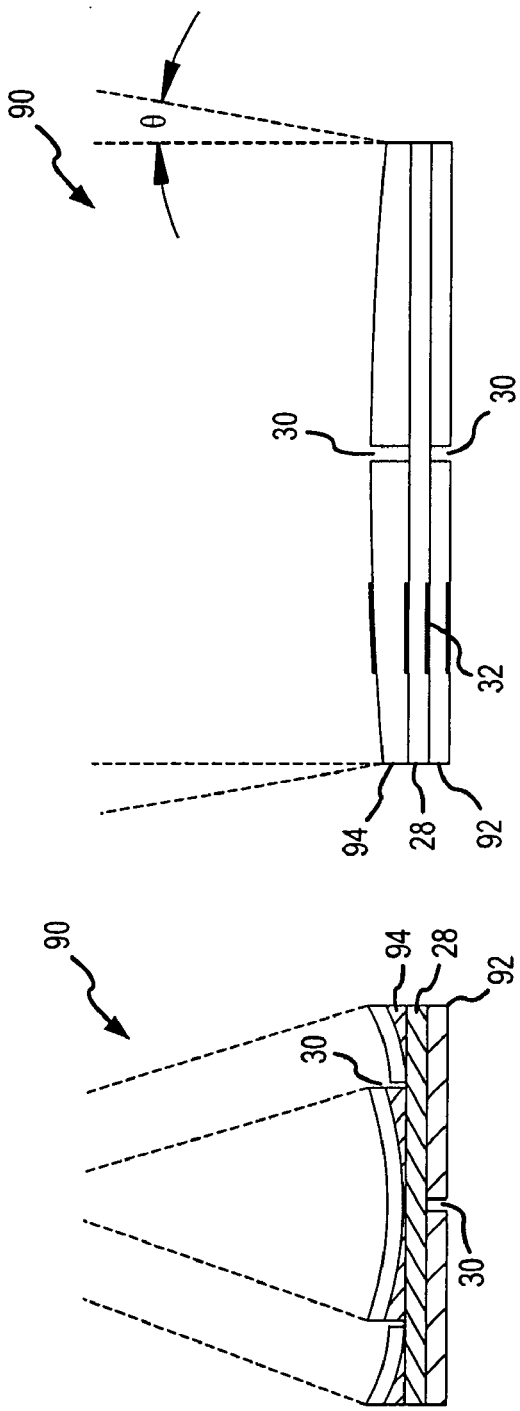
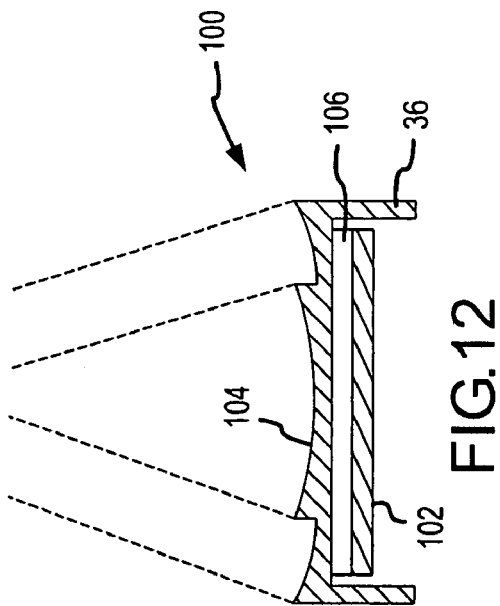

DEVICE AND METHOD FOR HIGH INTENSITY FOCUSED ULTRASOUND ABLATION WITH ACOUSTIC LENS

CROSS-REFERENCE TO RELATED APPLICATIONS

This application is related to U.S. application Ser. No. 11/646,526, filed 28 Dec. 2006, U.S. application Ser. No. 11/646,528, filed 28 Dec. 2006, U.S. application Ser. No. 11/642,923, filed 21 Dec. 2006, U.S. application Ser. No. 11/642,821, filed 21 Dec. 2006, U.S. application Ser. No. 11/647,295, filed 29 Dec. 2006, U.S. application Ser. No. 11/646,524, filed 28 Dec. 2006, and U.S. application Ser. No. 11/703,784, filed 8 Feb. 2007. The foregoing applications are hereby incorporated by reference in their entirety as though fully set forth herein.

BACKGROUND OF THE INVENTION a. Field of the Invention

The instant invention relates to ultrasound medical procedures. In particular, the instant invention relates to a lens-directed high intensity focused ultrasound (HIFU) transducer.

b. Background Art

High intensity focused ultrasound (HIFU) is a technique wherein thermal therapy is typically delivered to a patient in the form of a focused high power acoustic beam emanating from an acoustic transducer. The principle advantage of focusing in HIFU is that the heating beam can be focused to selectively treat tissue regions, including remote interior tissues. Thus, HIFU is actively being developed for many treatments, such as cardiac ablation to treat cardiac arrhythmia and the destruction of cancerous tissues at depth.

One challenge in the design of reliable HIFU transducers is placing the therapeutic heat at the desired location without allowing acoustic heating or secondary, loss-related heating to damage the transducer or non-targeted tissues or to interfere with the transducer's ongoing acoustic contact with tissue. Design of a HIFU transducer should therefore take into consideration both the heat created by the primary therapeutic acoustic energy directed upon or into the tissue and the waste heat generated in the transducer due to imperfect (e.g., less than 100%) electrical-to-acoustic energy conversion. One solution to this problem is to utilize a fluid-filled standoff membrane, which acts both as a physical acoustic standoff and as a thermal sink for heat near the transducer face. The fluid in the standoff may also be flowed or permitted to weep in order to further cool the tissue.

There are three possible options for the construction of HIFU transducers. First, a mechanically focused transducer, with a shaped piezoemitter, may be employed. Second, a lens-focused transducer, with a generally flat piezoemitter, may be employed. The term "lens" refers to an acoustically-redirecting entity through which acoustic energy passes and which provides a useful beam direction or reshaping, for example by focusing the acoustic energy to one or more distal foci. Finally, an electronically focused transducer, generally incorporating a generally flat piezoemitter, may be utilized. All three options may further include an optional acoustic matching layer.

Virtually all extant acoustically focused therapeutic and surgical transducers are mechanically focused utilizing shaped piezoemitters. Such transducers are easy to design, of very high electroacoustic efficiency because of the lack of acoustically lossy materials in the beam path, and have negligible beam side-lobes because they typically have only a single piezoelement. They are, however, quite expensive to manufacture due to the complexity involved in shaping and surface-finishing non-flat piezoelectric materials.

BRIEF SUMMARY OF THE INVENTION

Thus, it is desirable to be able to provide a relatively inexpensive HIFU transducer that utilizes a generally flat acoustic emitter acoustically coupled to a molded acoustic lens.

It is also desirable to be able to achieve acoustic focusing of HIFU ultrasound with minimal attenuation, and thus minimal thermal compromise to the HIFU transducer.

It is further desirable to alleviate the thermal-expansion mismatch stresses that arise in the transducer during operation in order to prevent delamination or decoupling of the acoustic lens from the acoustic emitter, or other undesirable thermal damage effects.

It is also desirable to provide a HIFU transducer that is relatively simple and economical to manufacture, and whose manufacture can be batched and/or automated.

Lensed transducers are potentially more economical to manufacture due to the relative simplicity of manufacturing a generally flat piezoemitter by comparison to a shaped piezoemitter, as well as the potential for cheaply molding a polymeric acoustic lens. However, because the acoustic power densities are quite high even at the transducer face and within an acoustic lens, it is clear that, if transducer focusing is to be provided by an acoustic lens, the lens should have near zero acoustic attenuation or it will melt, burn, or otherwise degrade. Further, due to the differing thermal expansion coefficients between the lens material and the piezoemitter material and/or matching layer material(s), thermal-expansion mismatch stresses may delaminate or otherwise decouple the lens from the acoustic emitter and/or matching layer(s). Other undesirable thermal effects are also prevalent, such as thermal expansion mismatch-induced fracture or cracking of the piezocomponents and lens eating, which can increase lens attenuation. The undesirable thermal effects are collectively referred to herein as "thermal degradation" or "thermal compromise" of the HIFU transducer.

According to a first embodiment of the invention, a high intensity focused ultrasound transducer includes: a first ultrasonic emitter having a first surface and a second surface opposite the first surface, the first ultrasonic emitter generating ultrasonic energy that propagates along a beam path from the first surface; at least one polymeric ultrasonic lens acoustically coupled to the first surface at least partially in the beam path of the ultrasonic energy propagating therefrom, such that the at least one polymeric ultrasonic lens can direct or shape the ultrasonic energy propagating from the first ultrasonic emitter in at least one direction; and at least one stress mitigation feature configured to mitigate thermal expansion mismatch stresses arising between the first ultrasonic emitter and the at least one polymeric ultrasonic lens during operation of the transducer. The transducer may operate at a frequency between about 1.5 MHz and about 50 MHz, and more preferably between about 2 MHz and about 30 MHz, while the ultrasonic energy preferably has an instantaneous power density between about 1000 W/cm$^2$ and about 5000 W/cm$^2$ at one or more points in the beam path. Such acoustic power densities at the acoustic focus are typical for thermal lesion-forming HIFU transducers.

At least one of, and optionally both of, the first surface will typically be either generally flat or monotonically curvilinear. Optionally, the first ultrasonic emitter may be either plano-concave or plano-convex. Typically, the first ultrasonic emitter is a piezoelectric element, such as a piezoceramic, PZT, a piezocomposite, or a piezopolymer, but it may also be an electrostrictive material, a magnetostrictive material, a ferroelectric material, an electrostatic element, a micromechanical element, a micro-electro-mechanical element, or a combination thereof. As described in further detail below, an optional stress mitigation layer, such as an acoustic matching layer, a thermally conductive layer, or a stress-buffering layer, may overlay the first surface, or, in some embodiments, the second surface.

The at least one ultrasonic lens may focus, collimate, defocus, or otherwise shape, direct, or redirect the emitted ultrasonic energy in at least one, and optionally in at least two, directions, and may, when focusing, direct the ultrasonic energy to a single focus or to a plurality of foci. For example, the lens may have a plano-concave cross section with respect to a cross-sectional cut along one axis or along two orthogonal axes. It may be either adjacent and directly coupled to the first ultrasonic emitter or spaced apart from the first ultrasonic emitter with an ultrasonic transmission medium, such as an ultrasonic transmission fluid, disposed between the lens and the emitter. Typical low-attenuation materials for the ultrasonic lens include polyetherimides, polyetheretherketones, crosslinked polystyrenes, polyolefins, and any combinations thereof. The at least one ultrasonic lens may be a unitary piece, and may be either simple (i.e., a single lens segment) or compound (i.e., multiple lens segments). One or more segments of the lens may be Fresnel segments, plano-concave segments, plano-convex segments, or convex-concave segments. To minimize thermal degradation and thermal compromise due to lens heating and/or expansion, the attenuation of the ultrasonic lens is preferably less than or equal to about 2 dB/cm-MHz, more preferably less than about 1.5 dB/cm-MHz, and most preferably less than about 1 dB/cm-MHz when measured at about room temperature.

Any orientation of the at least one ultrasonic lens relative to the first ultrasonic emitter that shapes or directs the emitted ultrasonic energy is contemplated. For example, the lens may be a Fresnel lens having a substantially flat surface and a structured surface opposite the substantially flat surface, either surface of which may be juxtaposed in face-to-face relationship with the first surface of the first ultrasonic emitter. Alternatively, the Fresnel lens may have a structured surface and a curvilinear surface opposite the structured surface, and either surface may be juxtaposed in face-to-face relationship with the first surface of the first ultrasonic emitter. Preferably, the angle at which the ultrasonic energy passes into and through the at least one polymeric ultrasonic lens is less than a critical acoustic angle above which large losses to shear modes occur, and the maximum thickness of the at least one polymeric ultrasonic lens is small enough to avoid thermal compromise to the transducer due to lens attenuative self-heating.

The transducer optionally includes a second ultrasonic emitter substantially identical to the first emitter, with the first and second ultrasonic emitters connected at an angle to deliver the ultrasonic energy to the tissue from different directions. This arrangement, although structurally more complex than a single ultrasonic emitter, advantageously allows for the use of thinner lenses and provides increased freedom as to allowable foci relative to the single emitter embodiment.

In some embodiments, the at least one polymeric ultrasonic lens includes a plurality of segments (or "lenslets"); a first segment of the at least one polymeric ultrasonic lens may be acoustically coupled to the first surface of the first ultrasonic emitter, and a second segment of the at least one polymeric ultrasonic lens may be acoustically coupled to the first surface of the second ultrasonic emitter. In other embodiments, the transducer includes at least two polymeric ultrasonic lenses; a first polymeric ultrasonic lens may be acoustically coupled to the first surface of the first ultrasonic emitter and a second ultrasonic lens may be acoustically coupled to the first surface of the second ultrasonic emitter.

An acoustic matching layer is optionally provided between the first ultrasonic emitter and the at least one polymeric ultrasonic lens to mitigate thermal expansion mismatch stresses. As will be described in further detail below, the term "mitigate" encompasses, without limitation, stress reduction, stress buffering, and stress avoidance. Preferably, the acoustic matching layer has an acoustic impedance intermediate to that of the first ultrasonic emitter and the at least one polymeric ultrasonic lens. The acoustic matching layer may be adjacent to and may directly acoustically couple the first ultrasonic emitter and the at least one polymeric ultrasonic lens.

The stress mitigation features, including, without limitation, stress-relieving kerfs, thermally conductive heat sink films or layers, and acoustically-passive stress buffer layers, may be provided anywhere in, on, or interleaved with the first ultrasonic emitter, the at least one polymeric ultrasonic lens, the acoustic matching layer, or a combination thereof. A thermally conductive film or layer may also be electrically conductive, so as to additionally serve as an electrode for the transducer.

Optionally, the transducer includes an acoustically transmissive membrane, which may include a urethane-based polymeric material, containing an ultrasonic transmission fluid or medium. The membrane may be disposed over the at least one polymeric ultrasonic lens or over the first ultrasonic emitter. The ultrasonic transmission fluid may be flowed in order to cool the transducer and/or tissue. The membrane and transmission fluid themselves may also serve to direct the ultrasonic energy. The ultrasonic transmission fluid may also flow through at least one channel within or defined by the at least one polymeric ultrasonic lens or another component of the transducer to provide emitter cooling, lens cooling, and/or transducer cooling.

An acoustic reflector material may be disposed adjacent the second surface of the first ultrasonic emitter to inhibit ultrasonic energy emissions from the second surface. The acoustic reflector typically includes a plurality of cavities or pores that are not transmissive of ultrasound, and may further include a gas layer or an air-like material layer disposed adjacent the second surface of the first ultrasonic emitter. Such materials have acoustic properties close to that of air, and thus inhibit "backwards" acoustic propagation.

An optional housing may enclose at least a portion of the first ultrasonic emitter. The at least one polymeric ultrasonic lens may be integrated into the housing. Such a housing may provide a sealed, dry environment for the transducer and its electrodes, as well as protection of patient and user from operational voltages.

According to another aspect of the invention, a method of ablating tissue includes the steps of: exciting at least one ultrasonic emitter to generate high intensity ultrasonic energy along a beam path, the high intensity ultrasonic energy having an instantaneous power density of at least about 1000 W/cm$^2$ at one or more locations within the beam path; directing the high intensity ultrasonic energy in at least one direction with at least one polymeric ultrasonic lens positioned in the beam path and acoustically coupled to the at least one ultrasonic emitter, the at least one polymeric ultrasonic lens having an attenuation less than about 2 dB/cm-MHz when measured at about room temperature; and delivering the directed high intensity ultrasonic energy to tissue to be ablated while using at least one stress mitigation feature to mitigate thermal expansion mismatch stresses arising between the at least one ultrasonic emitter and the at least one polymeric ultrasonic lens. The step of exciting at least one ultrasonic emitter may include exciting the at least one ultrasonic emitter to emit any of the following: high intensity ultrasonic energy at a frequency between about 2 MHz and about 7 MHz and a power of about 80 W to about 150 W, preferably at a frequency of about 3.5 MHz and a power of about 130 W; high intensity ultrasonic energy at a frequency between about 2 MHz and about 14 MHz and a power of about 20 W to about 80 W, preferably at a frequency of about 6 MHz and a power of about 60 W; and high intensity ultrasonic energy at a frequency between about 3 MHz and about 16 MHz and a power of about 2 W to about 20 W, preferably at a frequency of about 6 MHz and a power of about 15 W. During ablation, the temperature of one or more of the at least one ultrasonic emitter and the at least one ultrasonic lens may be directly or indirectly monitored and/or regulated to remain below a thermal damage point (that is, a point at which the transducer begins to experience undesirable thermal consequences). A temperature sensor, such as a thermocouple or thermistor, may be employed to monitor the temperature of the lens or other transducer component.

In still another embodiment of the present invention, a high intensity focused ultrasound tissue ablation device includes a plurality of transducers, and at least some of the plurality of transducers include: at least one ultrasonic emitter having a substantially flat first surface, wherein the at least one ultrasonic emitter generates ultrasonic energy that propagates along a beam path from the first surface, the ultrasonic energy having a power density of at least about 1000 W/cm$^2$ at one or more locations within the beam path; and at least one ultrasonic lens acoustically coupled to the first surface in the beam path of the ultrasonic energy propagating therefrom, such that the at least one ultrasonic lens can direct the ultrasonic energy in at least one direction in order to deliver it to the tissue to be ablated, and wherein an attenuation of the at least one ultrasonic lens is low enough to prevent thermal damage to the at least one ultrasonic lens during operation of the tissue ablation device. Thus, the transducers may include one or more kerfs, one or more heat sinks or thermally conductive features, one or more stress-buffering layers, one or more acoustic matching layers, or a combination thereof in order to mitigate thermal expansion mismatch stresses.

Optionally, the at least one ultrasonic lens spreads the high intensity ultrasonic energy in at least one direction such that energy emitted by adjacent ones of the plurality of transducers overlaps. This facilitates creation of a substantially continuous lesion, for example about at least a portion of a pulmonary vein.

Also disclosed herein is a high intensity focused ultrasound tissue ablation device including a plurality of transducers, at least some of which include: at least one ultrasonic emitter having a monotonically curvilinear first surface, wherein the at least one ultrasonic emitter generates ultrasonic energy that propagates along a beam path from the surface, the ultrasonic energy having a power density of at least about 1000 W/cm$^2$ at one or more locations within the beam path; and at least one ultrasonic lens acoustically coupled to the first surface in the beam path of the ultrasonic energy propagating therefrom, such that the at least one ultrasonic lens can direct the ultrasonic energy propagating from the first ultrasonic emitter in at least one direction in order to deliver it to tissue to be ablated, and wherein an attenuation of the at least one ultrasonic lens is low enough to prevent thermal damage to the at least one ultrasonic lens during operation of the tissue ablation device.

In still another embodiment of the invention, a high intensity focused ultrasound transducer includes: an ultrasonic emitter having a flat surface that emits high intensity ultrasonic energy along a beam path, the high intensity ultrasonic energy having a power density of at least about 1000 W/cm$^2$ at one or more locations within the beam path; and a liquid lens acoustically coupled to the ultrasonic emitter. The liquid lens includes a membrane covering the surface and an ultrasonic transmission fluid disposed between the membrane and the surface. The membrane is shaped such that, when the membrane is filled with the ultrasonic transmission fluid, the liquid lens focuses the ultrasonic energy emitted by the ultrasonic emitter. The ultrasonic transmission fluid may also be a gel, such that a "gel lens" is coupled to the ultrasonic emitter.

According to yet another aspect of the invention, a method of manufacturing a high intensity focused ultrasound transducer includes the steps of: providing at least one ultrasonic emitter having a surface capable of emitting high intensity ultrasonic energy along a beam path, the high intensity ultrasonic energy having a power density of at least about 1000 W/cm$^2$ at one or more locations within the beam path; providing at least one low attenuation polymeric ultrasonic lens configured to direct ultrasonic energy passing therethrough, the at least one low attenuation polymeric ultrasonic lens having an attenuation less than about 2 dB/cm-MHz when measured at about room temperature; and acoustically coupling the at least one polymeric ultrasonic lens to the at least one ultrasonic emitter such that the at least one polymeric ultrasonic lens can direct the high intensity ultrasonic energy emitted by the at least one ultrasonic emitter in at least one direction without thermally degrading. The surface may be substantially flat or monotonically curvilinear; if monotonically curvilinear, the surface may be manufactured as substantially flat and then bent into a monotonically curvilinear configuration. The lens may be molded, cast, thermoformed, or formed using other conventional methods, and the lens and emitter may be laminated together. At least one stress mitigation feature may be introduced into the transducer to avoid or otherwise mitigate thermal expansion mismatch stresses.

An advantage of the present invention is that it utilizes lower cost acoustic components having one or more surfaces that are at least manufactured as flat.

The foregoing and other aspects, features, details, utilities, and advantages of the present invention will be apparent from reading the following description and claims, and from reviewing the accompanying drawings.

BRIEF DESCRIPTION OF THE DRAWINGS

FIGS. 6a and 6b are, respectively, end and side views of a HIFU transducer according to one embodiment of the invention utilizing a plano-concave lens.

FIGS. 7a and 7b are, respectively, end and side views of a HIFU transducer according to a second embodiment of the invention utilizing a Fresnel plano-concave lens.

FIGS. 8a and 8b are, respectively, end and side views of a HIFU transducer according to another embodiment of the invention utilizing a rigid or semi-rigid shell-like lens, which includes a cavity containing an acoustically transmissive material.

FIGS. 9a and 9b are, respectively, end and side views of a HIFU transducer according to a fourth embodiment of the invention utilizing a rigid or semi-rigid shell-like lens with Fresnel features, which includes a cavity containing an acoustically transmissive material.

FIGS. 10a and 10b are, respectively, end and side views of a HIFU transducer according to still another embodiment of the invention that includes multiple ultrasonic emitters and acoustic lenses.

FIGS. 11a and 11b are, respectively, end and side views of a HIFU transducer according to yet a further embodiment of the invention that directs the ultrasonic energy in at least two directions.

FIG. 12 is an end view of yet another embodiment of the present invention illustrating the use of an intermediate stress-buffering or stress-shielding layer between the ultrasonic emitter and the ultrasonic lens.

DETAILED DESCRIPTION OF THE INVENTION

The present invention provides a high intensity focused ultrasound (HIFU)-capable transducer incorporating one or more acoustic lenses. The invention will be described first with reference to the general features of such a transducer, and then several embodiments will be described with greater particularity. Though the invention will be described in connection with HIFU applications, it is contemplated that the invention may also be practiced in non-HIFU applications, for example ultrasonic imaging applications.

Figure 1:
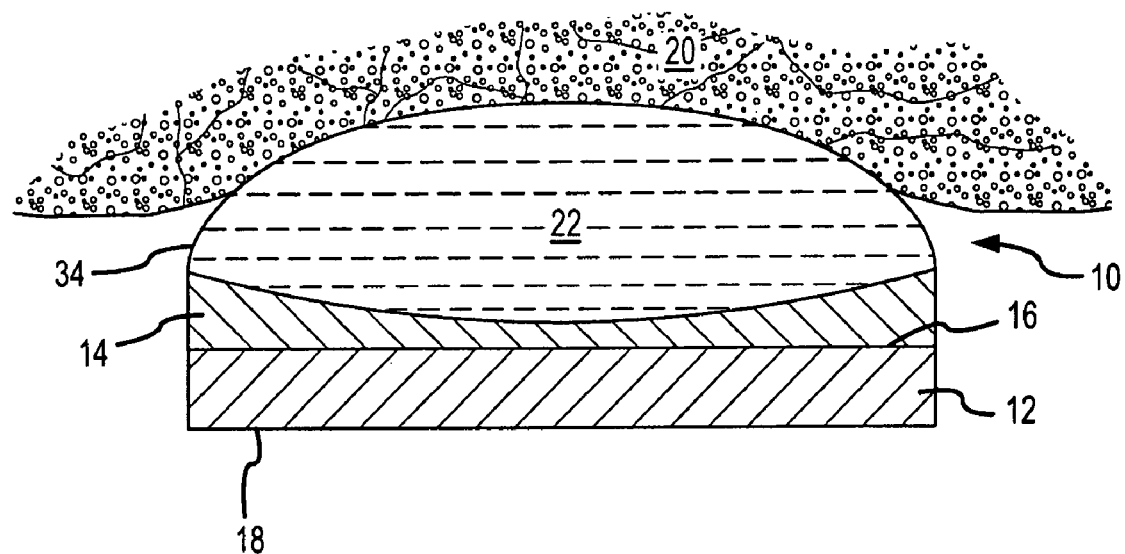
FIG. 1 depicts a cross-section illustrating some general features of a HIFU transducer according to the present invention.

FIG. 1 depicts an elevational cross-section of an exemplary HIFU transducer 10. HIFU transducer 10 generally includes a first ultrasonic emitter 12 that generates ultrasonic energy, at least one polymeric ultrasonic lens 14, and at least one stress mitigation feature that is configured to mitigate thermal expansion mismatch stresses arising between first ultrasonic emitter 12 and ultrasonic lens 14 during operation of HIFU transducer 10. HIFU transducer 10 typically operates at a frequency between about 1.5 MHz and about 50 MHz, and preferably between about 2 MHz and about 30 MHz in a pulsed or continuous wave manner.

The term "mitigate," as used herein, encompasses stress buffering, stress reduction, and stress avoidance. The term "stress buffering" refers to shielding or masking a stress such that it does not pass into a fragile component, for example as by inserting an intervening, durable stress-absorbing layer. "Stress reduction" refers to reducing stress at its source, for example as by providing stress relief features (e.g., kerfs or slots), reducing temperatures in a transducer having differing thermal expansion rates (for example, as by providing a thermally conductive layer), reducing thermal gradients, or choosing materials that have more closely matched thermal expansion behaviors.

First ultrasonic emitter 12 generally includes a first surface 16 and a second surface 18, which is opposite first surface 16. For purposes of this disclosure, the labels "first surface 16" and "second surface 18" are used to refer to the surfaces of first ultrasonic emitter 12 facing towards and away from a patient tissue surface 20, respectively; first surface 16 may also be thought of as the output face of first ultrasonic emitter 12, while second surface 18 may be thought of as the backside of first ultrasonic emitter 12. Thus, the ultrasonic energy generated by first ultrasonic emitter 12 propagates towards tissue surface 20 along a beam path emanating from first surface 16. Preferably, the ultrasonic energy has an instantaneous power density between about 1000 W/cm$^2$ and about 5000 W/cm$^2$ at one or more points along the beam path (one of skill in the art will appreciate that the time-averaged power may be lower), for example at one or more foci (as used herein, the terms "focus" and "foci" encompass both discrete focal points and larger focal regions, including, for example, focus along a line in space).

Typically, first ultrasonic emitter 12 is a piezoelectric element, such as a piezoceramic, lead-zirconate-titanate (PZT) monolithic polycrystalline or single-crystal slab, a piezopolymer material such as PVDF, or a polycrystalline or single-crystal piezocomposite material such as a diced PZT with polymeric-filled kerfs. It is also contemplated, however, that first ultrasonic emitter 12 may instead be an electrostrictive material, a magnetostrictive material, a ferroelectric material, a photoacoustic material, one or more electrostatic elements, one or more micromechanical elements, or one or more micro-electro-mechanical (MEM) elements. Combinations of any of the above are also contemplated.

First ultrasonic emitter 12 may take any of a number of shapes and configurations within the scope of the present invention. Preferably, first surface 16 is either substantially flat or monotonically curvilinear. In embodiments including a monotonically curvilinear first surface 16, first surface 16 may initially be formed substantially flat and then, during manufacture or assembly of HIFU transducer 10, may be deformed into a monotonically curvilinear configuration for use. Forming first surface 16 as substantially flat reduces the cost and complexity associated with the manufacture of first ultrasonic emitter 12, while introducing a monotonic curve facilitates, to an extent, mechanical direction of the ultrasonic energy generated by first ultrasonic emitter 12.

In the preferred embodiment of the invention, both first surface 16 and second surface 18 are substantially flat, thereby greatly reducing the cost and complexity associated with the manufacture of first ultrasonic emitter 12. In other embodiments, first ultrasonic emitter 12 is plano-concave (e.g., first surface 16 is substantially flat and second surface 18 is concave), while in still other embodiments, first ultrasonic emitter 12 is plano-convex (e.g., first surface 16 is substantially flat and second surface 18 is convex). As with a monotonically curvilinear first surface 16, use of a plano-concave or plano-convex first ultrasonic emitter 12 facilitates mechanical direction of the ultrasonic energy without significant adverse effects on the cost or complexity associated with the manufacture of first ultrasonic emitter 12. One of ordinary skill in the art will understand how to select an appropriate shape and material for first ultrasonic emitter 12 given a particular application of HIFU transducer 10.

Ultrasonic lens 14 is acoustically coupled to first surface 16 at least partially in the beam path (i.e., between first surface 16 and tissue surface 20) such that ultrasonic lens 14 can direct or redirect the ultrasonic energy propagating from first ultrasonic emitter 12 in at least one direction, for example to one or more foci, and, in some embodiments of the invention, in at least two directions, which may or may not overlap. Typical directions in which ultrasonic lens 14 directs the ultrasonic energy are the elevational (shown in FIG. 1) and/or azimuthal directions, though it is contemplated that the energy may be directed in one or more other directions as well. The terms "direct" and "redirect" include, but are not limited to, focusing the ultrasonic energy, collimating the ultrasonic energy, and spreading, homogenizing, or defocusing the ultrasonic energy.

Ultrasonic lens 14 may include a single lens segment (as shown in FIG. 1) or a plurality of lens segments. The term "lens segment" (or "lenslet") is used herein to refer to a portion of ultrasonic lens 14 capable of directing or redirecting at least some of the ultrasonic energy generated by first ultrasonic emitter 12 in at least one direction. Thus, ultrasonic lens 14 may be simple or compound. For a compound ultrasonic lens 14, it is contemplated that each lens segment may be formed as a unitary piece, and the plurality of lens segments thereafter arranged in acoustic communication with first ultrasonic emitter 12 to form ultrasonic lens 14. Preferably, however, ultrasonic lens 14 is formed in its entirety as a single piece, for example by molding, casting, or thermoforming, regardless of whether ultrasonic lens 14 is simple or compound, as a unitary ultrasonic lens 14 manufacturing process minimizes the cost and complexity associated with the manufacture of HIFU transducer 10, and may also permit simultaneous bulk manufacture of several ultrasonic lenses 14. It is also contemplated that ultrasonic lens 14 may be molded with a flat surface and bent or radiused during the assembly of transducer 10 such that the original flat surface becomes somewhat curved. It is also contemplated that ultrasonic lens 14 may be formed directly upon the acoustic components (e.g., ultrasonic emitter 12 and any matching layers), for example as by direct casting or molding.

Where distal focusing of the ultrasonic energy is desired, a compound ultrasonic lens 14 may be utilized to direct the ultrasonic energy to one or more foci. A compound ultrasonic lens 14 may also direct the energy to a single focus, and the energy may be directed to arrive in phase or out of phase—that is, the ultrasonic energy can arrive at a single point or along a single line on or within tissue 20 at different times and/or from different directions, depending on the particular application of HIFU transducer 10. A compound ultrasonic lens 14 may also be arranged wherein different subsets of lenslets or lens segments focus to different depths in the tissue along one or more spatial lines or surfaces.

An acoustically transmissive membrane 34, preferably made wholly or partly of a urethane-based thin flexible polymeric material a few mils or less thick, may be provided situated over ultrasonic lens 14, with an ultrasonic transmission medium 22 disposed between membrane 34 and ultrasonic lens 14. As generally known in the art, ultrasonic transmission medium 22 and membrane 34 acoustically couple HIFU transducer 10 to tissue 20, for example by providing a conformal wetted acoustic and thermal contact to tissue 20, and may also provide a standoff between HIFU transducer 10 and tissue 20. In addition, ultrasonic transmission medium 22 may be flowed to cool HIFU transducer 10 and/or tissue surface 20. Typically, transmission medium 22 will be saline or water. Membrane 34 may further include weep holes (not shown) through which ultrasonic transmission medium 22 may purposely leak, for example to allow wetting and/or cooling fluid to flow upon the surface of tissue 20. As an alternative to an enclosing membrane, ultrasonic transmission medium 22 may be laterally retained, but not necessarily completely enclosed, within an edge-defined water dam (not shown), which advantageously avoids any attenuation due to membrane 34. It is also contemplated that transmission medium 22 or another coolant may flow through passages within or defined by ultrasonic lens 14 or another component of transducer 10 (e.g., through flow passages in emitter 12). Such cooling, of course, reduces the temperatures within transducer 10, thereby mitigating thermal mismatch stresses and staving off thermal compromise and thermal degradation.

Figure 2:
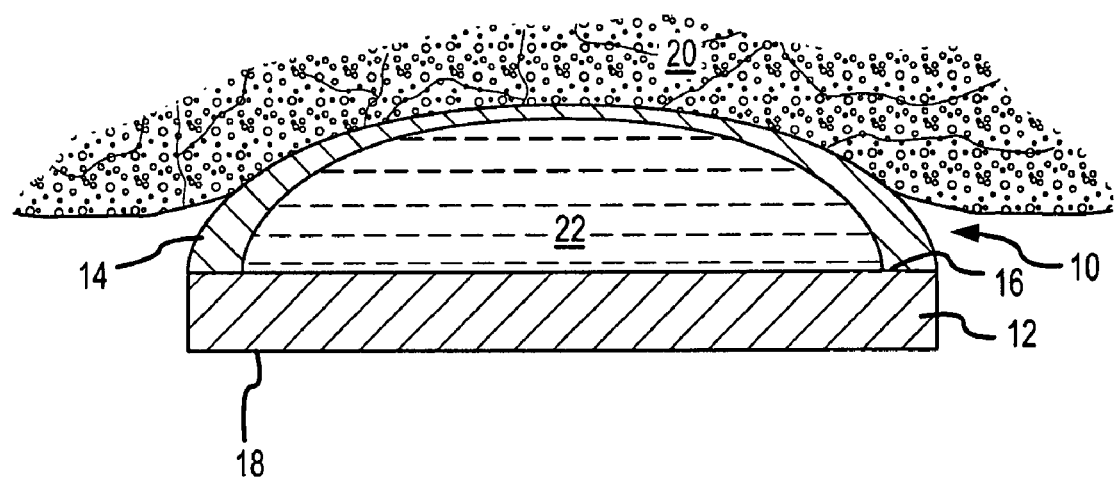
FIG. 2 illustrates additional general features of a HIFU transducer according to the present invention.

As one of ordinary skill will recognize, the manner in which ultrasonic lens 14 directs or redirects the ultrasonic energy passing therethrough depends upon not only the shape and orientation of ultrasonic lens 14, but also upon the acoustic velocity of the material or materials from which ultrasonic lens 14 is made. Accordingly, it is contemplated that segments of ultrasonic lens 14 may be plano-convex, plano-concave, convex-concave (e.g., shell-shaped, such as shown in FIG. 2), meniscus, convex-convex, concave-concave, or any combinations thereof, either face of which may be facing tissue 20 or emitter 12 without departing from the spirit and scope of the present invention. Further, in addition to fixed-radius lenses, parabolic, hyperbolic, and cylindrical lenses are also contemplated.

Ultrasonic lens 14 may have one or more discrete focal points or one or more spatially extended focal regions. Further, these different foci may be achieved not only by shaping and selection of the lens material, but also by frequency-changing methods wherein the focus location is a function of driving frequency; either or both of ultrasonic lens 14 or emitter 12 may have such a dependence.

As will be discussed in further detail below, ultrasonic lens 14 may be mechanically coupled (e.g., bonded) to emitter 12, or may be acoustically coupled to emitter 12 by ultrasonic transmission medium 22, an approach which facilitates physically changeable lenses for a given emitter.

Suitable materials for ultrasonic lens 14 include, but are not limited to, polyetherimides, polyetheretherketones, crosslinked polystyrenes, polyolefins, and any combinations thereof, all of which have quite low attenuation loss. Ultem®, a General Electric polymer, is well-suited for use in ultrasonic lens 14, insofar as it has an attenuation that is low at room temperature and that does not increase with temperature. Preferred materials include, without limitation, Ultem 1000 and Ultem 1000EF.

One of ordinary skill will understand how to select an appropriate shape and material for ultrasonic lens 14 and orient the lens relative to first ultrasonic emitter 12 given a particular application of HIFU transducer 10 and a desired beam shape. For example, a low velocity plano-convex lens or a high velocity plano-concave lens may be used to focus the ultrasonic energy, while a low velocity plano-concave lens or a high velocity plano-convex lens may be used to spread the ultrasonic energy, though the invention is not limited to these configurations.

Ultrasonic lens 14 may be positioned adjacent and directly acoustically coupled (i.e., mechanically coupled) to first ultrasonic emitter 12, as shown in FIG. 1. The embodiment of FIG. 1 shows that ultrasonic lens 14 may be mechanically coupled to first ultrasonic emitter 12 along substantially its entire length and width. Alternatively, as shown in FIG. 2, at least a portion of ultrasonic lens 14 may be spaced apart from and indirectly acoustically coupled to first ultrasonic emitter 12, with a suitable ultrasonic transmission medium 22, such as water, saline, or gel, disposed between first ultrasonic emitter 12 and the spaced-apart portion of ultrasonic lens 14. Thus, in the embodiment of FIG. 2, ultrasonic lens 14 is directly mechanically and acoustically coupled to first ultrasonic emitter 12 over only a relatively small distance and is mechanically decoupled along the rest of its length; optionally, HIFU transducer 10 may be constructed such that ultrasonic lens 14 is not mechanically coupled to first ultrasonic emitter 12 at all. Certain advantages of the spaced apart configuration illustrated in FIG. 2 will be explained in further detail below.

Preferably, ultrasonic lens 14 has low attenuation at both room temperature and elevated temperatures (e.g., operating temperatures), such that attenuative self-heating does not thermally damage or thermally degrade HIFU transducer 10, first ultrasonic emitter 12, or ultrasonic lens 14, or cause unintended burning of nearby tissue 20. Undesirable thermal damage and degradation includes, but is not limited to, significant softening or glass-transition of ultrasonic lens 14 in a manner causing acoustic or mechanical disruption, thermal mismatch breakage of any component, thermal mismatch delamination of any component, interfacial bond failure between components, permanent increases in lossiness or attenuation due to delamination or bubbling of an interlayer bonding material, thermal depoling of the piezomaterial, and other significant irreparable changes in the operating parameters of HIFU transducer 10. Another advantage of a low attenuation ultrasonic lens 14 is that a greater percentage of the ultrasonic energy generated by first ultrasonic emitter 12 will reach tissue 20 for treatment. Accordingly, ultrasonic lens 14 preferably has an attenuation, measured at about room temperature and about 2 MHz, less than or equal to about 2 dB/cm-MHZ, more preferably less than or equal to about 1.5 dB/cm-MHz, and most preferably less than or equal to about 1 dB/cm-MHz.

It is desirable to minimize the acoustic attenuation of ultrasonic lens 14 such that, for a given lens design, a minimum of attenuative heat will be generated in ultrasonic lens 14. By choosing a low attenuation material, such as Ultem®, it is possible to minimize a maximum thickness of the lens, thereby also minimizing the resulting maximum thermal mismatch stress between the lens and the emitter.

In terms of potential thermal degradation and thermal compromise, it is also desirable to avoid excessive conversion of ultrasonic compressive waves to shear waves and therefore heat—the acoustic analogue to total internal reflection and total attenuation in an optical lens. Thus, the angle at which the ultrasonic energy generated by first ultrasonic emitter 12 passes into and through ultrasonic lens 14 is preferably less than the known critical angle for the material of ultrasonic lens 14. As one of ordinary skill in the art should appreciate, the critical angle may be determined experimentally.

Figure 3:
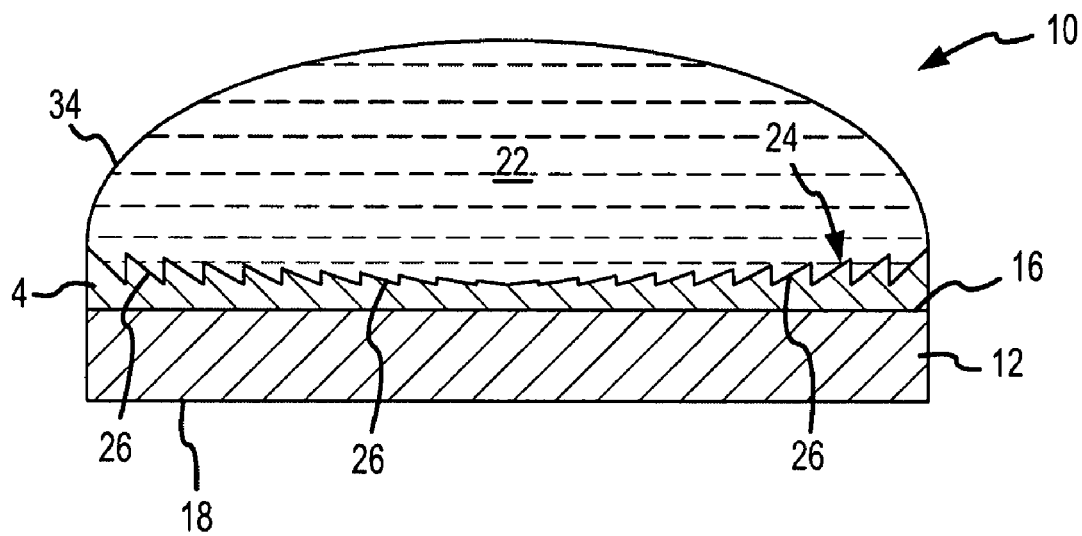
FIG. 3 is a cross-section of a HIFU transducer utilizing a Fresnel acoustic lens.

As ultrasonic lens 14 becomes thicker, its total path attenuation increases. Thus, it is also desirable to minimize the average and maximum thicknesses of ultrasonic lens 14, at least within the beam path of the ultrasonic energy, to further reduce attenuation and heating. For example, to reduce the average and maximum thicknesses of ultrasonic lens 14 of FIG. 1 designed for a specific focal distance, the lens may be segmented into Fresnel features or segments, as shown in FIG. 3. A Fresnel lens 14 reduces the thickness of the lens relative to a more traditional, non-Fresnel lens (that is, a plano-concave Fresnel lens is thinner than an ordinary plano-concave lens). The reduced thickness of the Fresnel lens configuration of FIG. 3 reduces the acoustic attenuation of ultrasonic lens 14, and therefore the likelihood of thermally damaging HIFU transducer 10 during operation, while simultaneously increasing the fraction of the ultrasonic energy delivered to tissue surface 20.

As can be understood by analogy to the optical arts, at least one surface 24 of a Fresnel lens is a structured surface, which may be formed by building protrusions upon or cutting grooves into a substantially flat lens surface. Advantageously, structured surface 24 may also function as a thermal radiator, particularly if a fluid, such as ultrasonic transmission fluid 22, is adjacent and/or flowed past structured surface 24. Such flow also advantageously sweeps any bubbles out of structured surface 24. The opposite surface of the Fresnel lens may be substantially flat, curvilinear, or also structured. FIG. 3 shows the opposite surface as flat and bonded to emitter 12. Depending upon the application of HIFU transducer 10, either surface may be juxtaposed in face-to-face relation with first surface 16 of first ultrasonic emitter 12. If desired, a suitable deformable or flowable ultrasonic transmission medium, such as urethane, water, or gel, may be disposed between first surface 16 and the facing surface of the Fresnel lens, for example where it is desired to flow such coolant between emitter 12 and lens 14, or where it is desired to avoid rigidly mechanically bonding lens 14 to emitter 12.

Any number of Fresnel elements 26 (three of which are labeled in FIG. 3) may be incorporated into ultrasonic lens 14. As the number of Fresnel elements 26 increases, the overall thickness of ultrasonic lens 14 will generally decrease, which also decreases the average and maximum attenuation of ultrasonic lens 14. In addition, as the number of Fresnel elements 26 increases, the complexity of structured surface 24 may decrease, since the shape of structured surface 24 may be approximated with straight-edged, rather than curved, elements 26. An upper limit on the number of Fresnel segments may be dictated by the desirability of having such segments be smaller than the wavelength of ultrasound in the lens material. For example, about 5 segments may be used for the lower frequencies of about 3 to about 7 MHz, while between about 7 to about 10 Fresnel segments may be used at higher frequencies.

Heat transfer capacity away from transducer 10 or tissue 20 may be further enhanced by flowing a fluid over, around the edges of, or through HIFU transducer 10. In some embodiments of the invention, the fluid flows through at least one lens-segment channel within or defined by ultrasonic lens 14. Dedicated non-focusing lens channels for coolant flow may also be provided. Ultrasonic lens 14 may also include one or more pores, permeations, or permeability through which fluid may pass or wick, for example to deliver cooling and/or acoustic coupling to the tissue/lens interface. It should be understood that cooling of the lens surface or tissue/lens interface also causes at-depth cooling in tissue 20 by outward thermal conduction from tissue 20 towards transducer 10. Such tissue and interface cooling can be beneficial if one desires, at a particular point in an ablation procedure, to assure that all thermal damage is subsurface in nature. It is within the scope of the invention to control the flow of fluid to beneficially manipulate the temperature of either or both of transducer 10 and tissue 20.

Ultrasonic lens 14 will have a non-zero, positive total integrated attenuation, and thus HIFU transducer 10 will heat during operation, for example via backwards thermal conduction from lens 14, thereby potentially generating mechanical stresses as first ultrasonic emitter 12 thermally expands and/or contracts to a different extent or at a different rate than ultrasonic lens 14. Typically, a polymeric ultrasonic lens 14 will desire to expand upon heating more than emitter 12, thereby putting emitter 12 in tension and potentially causing cracking, fracture, or warpage. In addition, the interfacial bond between emitter 12 and lens 14 at the interface is stressed, and could also delaminate or fail, as opposed to either or both of emitter 12 and lens 14 breaking. There are two primary sources of such stresses: (i) differing thermal expansion coefficients between first ultrasonic emitter 12 material(s) and ultrasonic lens 14 material(s); and (ii) thermal gradients entirely within one or more of ultrasonic emitter 12 material(s) and ultrasonic lens 14 material(s). In steady state operation, source (i) is typically the problem, whereas source (ii) is typically the problem during pulsed operation of HIFU transducer 10. Use of more thermally conductive components and the use of coolant may help mitigate thermal mismatch stresses. In addition, the use of ramped-up power, rather than a delta-function, may also beneficially reduce transient peak stresses.

Figure 4:
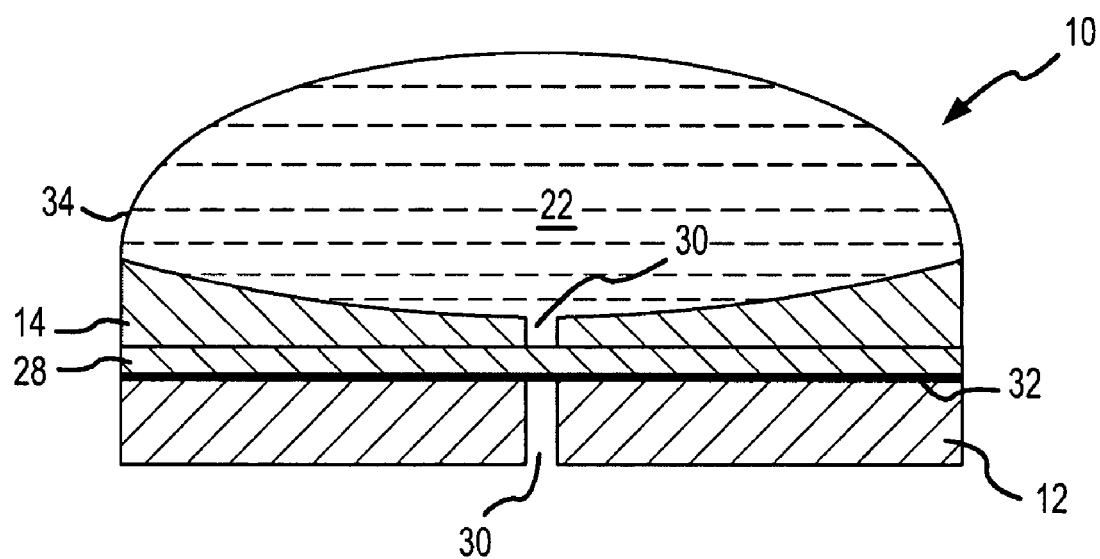
FIG. 4 illustrates a HIFU transducer incorporating a stress mitigation layer, kerfs, and thermally conductive films as thermal expansion mismatch stress mitigation features.

The present invention contemplates a number of design features, illustrated in FIG. 4, that may be implemented to mitigate such stresses. As shown in FIG. 4, HIFU transducer 10 may include one or more stress mitigation layers 28 (one such layer 28 is shown in FIG. 4), which may include, without limitation, acoustic matching layers, antimatching layers, foundation layers, thermally conductive layers, or acoustically-passive stress-buffering layers. Of course, a single layer 28 may fulfill more than one purpose (e.g., a layer that is both an acoustic matching layer and a stress-buffering layer, or a layer that is both a thermally conductive layer and a foundation layer).

Layers 28 are preferably selected and configured to mitigate thermal expansion mismatch stresses arising between first ultrasonic emitter 12 and ultrasonic lens 14 during operation of HIFU transducer 10. For example, a rigid and strong acoustic matching layer or a rigid and strong passive buffer layer (e.g., a material that is not easily stress-damaged, or strained, such as ceramic, glass, or low-expansion metal) effectively mechanically shields first ultrasonic emitter 12 from ultrasonic lens 14, thereby buffering any thermal expansion mismatch stresses that arise and reducing the risk of cracking first ultrasonic emitter 12 or debonding first ultrasonic emitter 12 and ultrasonic lens 14. Preferably, a buffer layer (whether or not the buffer layer is also an acoustic matching layer) has a coefficient of thermal expansion that is between the thermal expansion coefficients of ultrasonic lens 14 and emitter 12. More preferably, the coefficient of thermal expansion of a buffer layer is about equal to the coefficient of thermal expansion of first ultrasonic emitter 12. A buffer layer typically has a sufficiently high fracture toughness to withstand the stresses that arise in HIFU transducer 10 during operation.

Layer 28 is preferably thermally conductive in order to convey thermal energy away from either or both of first ultrasonic emitter 12 and ultrasonic lens 14, thereby reducing thermal expansion mismatch stresses by reducing heating, and thus the amount of thermal expansion stress coupled between first ultrasonic emitter 12 and ultrasonic lens 14. More preferably, layer 28 is more thermally conductive than first ultrasonic emitter 12 and ultrasonic lens 14.

A preferred material for layer 28 is aluminum nitride, which is a highly thermally conductive, low expansion material that can serve as an acoustic matching layer, a thermally conductive layer, and also as a stress-buffering layer. The following table provides the thermal properties of some suitable layers 28 as compared to the materials for emitter 12 and ultrasonic lens 14:

| Material | α in/in/C | K W/m-K |
| --- | --- | --- |
| Vitr Carbon | 2.5~3.5 × 10$^{-6}$ | 4.6~6.3 |
| Alumina | 6.7 × 10$^{-6}$ | 37 |
| Glass | 10.48 × 10$^{-6}$ | 1.38 |
| AlN | 4.6 × 10$^{-6}$ | 175 |
| SiC | 3.7 × 10$^{-6}$ | 272 |
| Macor | 9.3 × 10$^{-6}$ | 1.46 |
| PZT (emitter) | 3.8~4.5 × 10$^{-6}$ | 1.1 |
| Ultem ® 1000 (lens) | 54 × 10$^{-6}$ | 0.22 |

As illustrated in FIG. 4, layer 28 acoustically couples ultrasonic lens 14 to first ultrasonic emitter 12. Layer 28 may be directly acoustically and mechanically coupled via bonding, or joining, analogous to FIG. 1, or indirectly via a transmissive spacer of standoff material, such as ultrasonic transmission medium 22, analogous to FIG. 2. That is, layer 28 may be adjacent to or spaced apart from either or both of ultrasonic lens 14 and first ultrasonic emitter 12. Where layer 28 is an acoustic matching layer, it will typically have an acoustic impedance intermediate to the acoustic impedances of first ultrasonic emitter 12 and ultrasonic lens 14.

Those familiar with acoustic design will realize that one could alternatively implement backside (e.g., second surface 18) antimatching or reflective layers (not shown) or metallic mass-load layers, which are placed to remove heat or to provide a rigid foundation for emitter 12. Most favorably, any appreciably thick metal layer, whether frontside or backside, will be thermally conductive and of modest expansion coefficient. Invar™ and Kovar™ nickel-iron based alloys are suitable for this purpose. Of course, in addition to providing a stable flat or shaped surface to emitter 12, a foundation layer may also provide one or more of a heat removal path, an acoustic matching layer, an antimatching layer, an attenuative backer, or an electrode.

Typical materials for an acoustic matching layer include, but are not limited to, aluminum nitride, boron nitride, silicon nitride, graphite, vitreous carbon, silicon carbide, cermets, glasses, some metals, and some polymers, as well as mixtures or composites thereof. Thermally and/or electrically conductive microparticles or nanoparticles may also be used, particularly as dispersed or mixed into a composite material matching layer that is polymer, glass, ceramic, or metal-matrix based. Lens 14 and layer 28 might also be combined as a premade laminate of two different materials or compositions, yielding a configuration looking similar to that illustrated in FIGS. 1 and 3 after assembly. One of ordinary skill in the art will understand how to select and configure one or more suitable layers 28, such as acoustic matching layers, antimatching layers, foundation layers, thermally conductive layers, and stress-buffering layers for a particular application of HIFU transducer 10.

The accumulated stress in a thermally mismatched interface of two materials, such as the direct-bonded interface between first ultrasonic emitter 12 and ultrasonic lens 14 in FIG. 3, is proportional to the accumulated distance over which that mismatch exists, in addition to being generally proportional to the temperature and the intrinsic expansion mismatch per unit temperature itself. Thus, one or more stress relief kerfs 30 (FIG. 4) may be provided in first ultrasonic emitter 12 and/or ultrasonic lens 14. For purposes of this disclosure, a "kerf" is any disruption of an otherwise contiguous span of material, and reduces stress by reducing the accumulated distance over which thermal mismatch exists within HIFU transducer 10. Any number of kerfs 30, in any direction, may be employed. By appropriately locating kerfs 30 within HIFU transducer 10, thermal mismatch stresses may be mitigated (e.g., relieved) without significantly compromising acoustic and thermal performance. Preferably, layers 28 also serve as a stress-mitigating (e.g., stress buffering) backbone for HIFU transducer 10, and thus does not include kerfs, but it is within the scope of the invention to include kerfs in layers 28 in addition to or instead of kerfs in either or both of first ultrasonic emitter 12 and ultrasonic lens 14. It should be understood that the term "kerf," as used herein, is not limited to a dicing cut in a transducer, but rather refers to any disruption in material, whether created additively (e.g., by juxtaposing lens or emitter segments with intermediate gaps) or subtractively (e.g., by cutting into the lens or the emitter).

FIG. 4 illustrates kerfs 30 located generally centrally to transducer 10 along the azimuthal direction. Frequently, one will choose to bisect or trisect the overall length of transducer 10.

Thermally-induced expansion mismatch stresses may be further mitigated through the use of a heat sink feature, such as one or more thermally conductive layers 28 or films 32, shown in FIG. 4, disposed to conduct heat outwardly from an interior region of HIFU transducer 10. Thermally conductive films 32 or layers 28 reduce the magnitude of thermal gradients within HIFU transducer 10 and/or reduce the peak temperature of HIFU transducer 10. Films 32 may be electroplated, evaporated, or sputtered, or may be interleaved metal foils such as those used in flexible circuits. Preferably, however, thermally conductive films 32 are deposited using physical or chemical vapor deposition techniques. Films 32 are preferably more conductive thermally than emitter 12 and ultrasonic lens 14.

Thermally conductive films 32 may be provided on numerous interior or exterior surfaces of HIFU transducer 10 or any of its layers/components, including, but not limited to, first and second surfaces 16, 18 of first ultrasonic emitter 12 and either face of ultrasonic lens 14. In addition to being thermally conductive, films 32 may also be electrically conductive, such that they may also serve as electrodes for first ultrasonic emitter 12, electrically insulative, or partially electrically conductive and partially electrically insulative. One of ordinary skill in the art will also appreciate that suitably configured films 32 may replace one or more layers 28.

In some embodiments of HIFU transducer 10, either or both of membrane 34 and ultrasonic transmission medium 22 disposed therein may contribute to directing or redirecting the ultrasonic energy generated by first ultrasonic emitter 12. That is, either or both of membrane 34 and ultrasonic transmission medium 22 disposed therein may serve as a "liquid lens" or "gel lens" (if ultrasonic transmission medium 22 is a gel) that focuses, collimates, or defocuses the ultrasonic energy. Suitable fluids for such a "liquid lens" include, but are not limited to, fluoropolymeric liquids and perfluorocarbon liquids. Preferably, such a fluid would likely be circulated or captured in a closed enclosure rather than permitted to flow into the patient.

Figure 5:
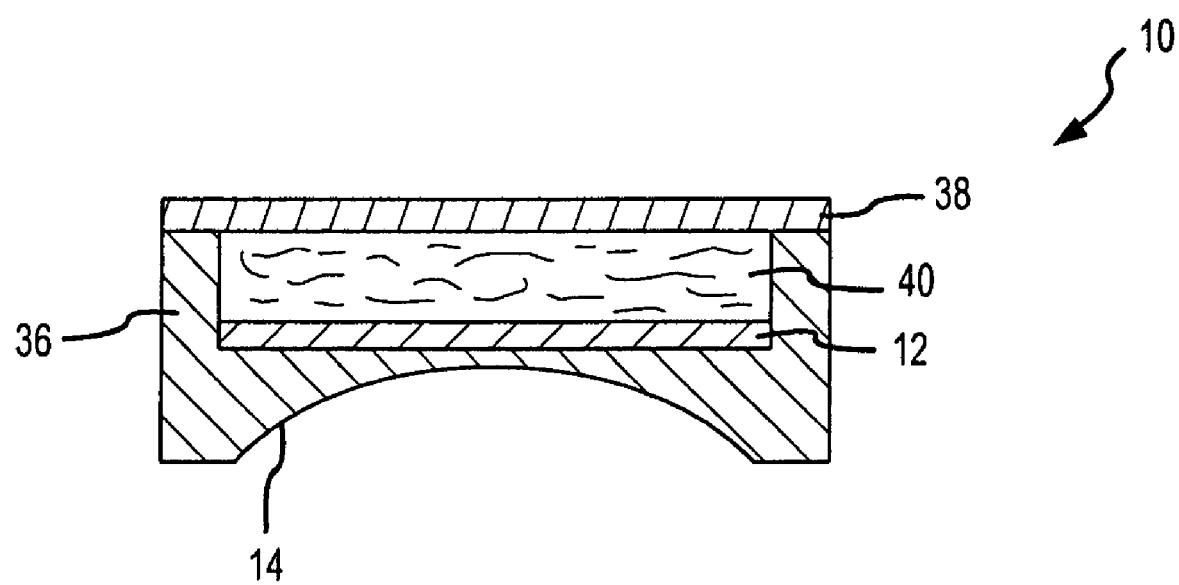
FIG. 5 illustrates a HIFU transducer with an enclosed ultrasonic emitter.

Referring now to FIG. 5, a housing 36 is shown enclosing at least a portion of first ultrasonic emitter 12. As shown, ultrasonic lens 14 is integrated with housing 36, though it is also contemplated that housing 36 may be formed separately from ultrasonic lens 14. Housing 36 seals first ultrasonic emitter 12 from water and other fluids and includes a cover 38 sealed to housing 36. Although the exterior surfaces of housing 36 are shown as generally flat and parallel to each other, they may have any shape without departing from the spirit and scope of the present invention. It is a manufacturing advantage to be able to mold the lens and the housing as one entity. It is also within the spirit and scope of the invention to mold lens 14 in any manner that includes other functional features of a transducer 10, for example a compound lens 14 that is molded to house multiple emitters 12.

An acoustic reflector 40 may be provided adjacent second surface 18 of first ultrasonic emitter 12. Acoustic reflector 30 inhibits ultrasonic energy emissions from second surface 18 (that is, propagating away from tissue 20), thereby increasing the operational efficiency of HIFU transducer 10. In general, acoustic reflector 40 includes one or more materials that are not transmissive of ultrasound, such as gas- or air-filled gaps, pores, or cavities, unwettable pseudo-air foams, and vacuum, any of which may be sealed against second surface 18 within housing 36 if desired. In addition to inhibiting "backwards" acoustic propagation, an unwettable pseudo-air foam advantageously prevents fluid ingress into transducer 10 without requiring transducer 10 to be hermetically sealed, which in turn reduces the cost of manufacturing transducer 10.

Certain specific embodiments of a HIFU transducer will now be described with reference to FIGS. 6-12. One of ordinary skill in the art will appreciate that additional combinations of the various elements, features, and orientations disclosed herein are possible, and will understand how to select and orient the various elements and features described in designing a transducer for a particular application. Thus, the embodiments of the present invention may include any number or combination of the foregoing design aspects.

FIG. 6a illustrates an end (azimuthal) view of a HIFU transducer 60, while FIG. 6b illustrates HIFU transducer 60 in side (elevational) view. HIFU transducer 60 includes a single substantially flat ultrasonic emitter 62 and a single plano-concave ultrasonic lens 64 directly acoustically and mechanically coupled thereto. Acoustic matching layer 28 couples ultrasonic emitter 62 to ultrasonic lens 64. To mitigate thermal expansion mismatch stresses arising in HIFU transducer 60, both ultrasonic emitter 62 and ultrasonic lens 64 include kerfs 30 in both the elevational and azimuthal directions. Kerfs 30 cut ultrasonic emitter 62 and ultrasonic lens 64 substantially in half both azimuthally and elevationally, but do not substantially penetrate acoustic matching layer 28, such that acoustic matching layer holds HIFU transducer 60 together. Kerfs 30, if narrow (e.g., a few mils wide), do not have a significant effect on the ability of ultrasonic lens 64 to direct ultrasonic energy, as they are small relative to the overall size of ultrasonic lens 64.

In addition, a plurality of thermally conductive films 32, shown in FIG. 6a, are provided on several surfaces within HIFU transducer 60, including both faces of ultrasonic emitter 62 and both faces of ultrasonic lens 64, in order to conduct heat outwardly from HIFU transducer 60. As shown with dashed lines in FIGS. 6a and 6b, the ultrasonic energy generated by ultrasonic emitter 62 is focused by ultrasonic lens 64 in the elevational plane (FIG. 6a) to create a line of focus in the azimuthal plane (FIG. 6b), and this is referred to as "cylindrically focused" along the azimuthal direction.

FIGS. 7a and 7b illustrate a HIFU transducer 60' according to a preferred embodiment of the invention that is functionally analogous to HIFU transducer 60. However, plano-concave ultrasonic lens 64 has been replaced by a plano-concave Fresnel ultrasonic lens 64' that includes three Fresnel elements 26 arranged in the elevational plane. To minimize the effect of kerfs 30 on direction of the ultrasonic energy, kerfs 30 are preferably placed at the junction between Fresnel elements 26. The average thickness of Fresnel ultrasonic lens 64' is less than the average thickness of ultrasonic lens 64, thereby lowering total acoustic attenuation, generating less total lens-attenuative heat, and reducing thermal expansion mismatch stresses arising between ultrasonic emitter 62 and Fresnel ultrasonic lens 64' of FIGS. 7a and 7b relative to those arising between ultrasonic emitter 62 and ultrasonic lens 64 of FIGS. 6a and 6b. Assuming that the Fresnel segments retain the surface curvature of the original lens 64 would focus in the same manner as lens 64. Of course, as one of ordinary skill in the art will appreciate, any lens can be configured to direct or redirect the ultrasonic energy as desired.

FIGS. 8a and 8b illustrate a HIFU transducer 70 where the ultrasonic energy generated by ultrasonic emitter 72 is directed by a shell-like convex-concave ultrasonic lens 74. Typically, lens 74 would have a convex radius different from its concave radius and thus variable thickness to provide focusing action. As shown in dashed lines in FIGS. 8a and 8b, the ultrasonic energy is focused along the azimuthal direction to create a line of focus in the azimuthal plane. As best shown in FIG. 8a, a portion of convex-concave ultrasonic lens 74 is indirectly acoustically coupled to ultrasonic emitter 72 via ultrasonic transmission medium 22 disposed between ultrasonic lens 74 and acoustic matching layer 28; ultrasonic lens 74 is only mechanically coupled and directly acoustically coupled to acoustic matching layer 28 over relatively short lengths 76a, 76b, which are preferably, but not necessarily, peripheral to the beam path. By substantially mechanically decoupling ultrasonic lens 74 from ultrasonic emitter 72, the effect of accumulated interfacial thermal expansion mismatch stresses is effectively limited to lengths 76a, 76b. Further, since lengths 76a, 76b are preferably peripheral to the beam path, the mechanical coupling between ultrasonic lens 74 and ultrasonic emitter 72 may be arranged to be elastic or lossy in order to further mitigate thermal expansion mismatch stresses. Further mitigation of harmful thermal effects may be provided by flowing ultrasonic transmission medium 22.

FIGS. 9a and 9b illustrate a HIFU transducer 70' according to another preferred embodiment of the invention that is functionally analogous to HIFU transducer 70 as described in connection with FIGS. 8a and 8b. However, convex-concave ultrasonic lens 74 has been replaced by a focus-equivalent convex-concave Fresnel ultrasonic lens 74' that includes three Fresnel elements 26. Thus, HIFU transducer 70' is to HIFU transducer 70 as HIFU transducer 60' is to HIFU transducer 60.

FIGS. 10a and 10b illustrate a HIFU transducer 80 that incorporates two ultrasonic emitters 82a, 82b, each with a corresponding plano-concave ultrasonic lens 84a, 84b acoustically coupled thereto. Ultrasonic emitters 82a, 82b are angled relative to each other. Preferably, this angle is between about 5 degrees and about 45 degrees, more preferably between about 20 degrees and about 35 degrees. As shown in dashed lines, emitters 82a, 82b are each cylindrically focused in the elevation plane along the azimuthal direction. Ultrasonic emitters 82a, 82b can be activated to deliver ultrasonic energy to the focus or foci either in phase or out of phase. Typically, the two focal lines of emitters 82a, 82b will be arranged to overlap in space. One of ordinary skill in the art will appreciate that HIFU transducer 80 could also be modified such that ultrasonic lenses 84a, 84b are replaced by equivalent Fresnel lenses. Further, though FIGS. 10a and 10b illustrate independent ultrasonic lenses 84a, 84b coupled to ultrasonic emitters 82a, 82b, it is contemplated that one could mold the two lenses 84a, 84b as a single, contiguous entity (not shown).

An intrinsic acoustic advantage of the device illustrated in FIGS. 10a and 10b is that each lens 84a, 84b needs to individually redirect the beam in the elevation plane to a lesser amount than would a single emitter/lens transducer of equal total elevation width focused at the same depth. Thus, lenses 84a, 84b can be thinner and run cooler, and therefore be less thermally stressed. Acoustic practitioners will also recognize that the device of FIGS. 10a and 10b provides two independent means of forming a focus-tilt angle and lens design-leading to improved flexibility.

FIGS. 11a and 11b illustrate, respectively, elevational and azimuthal views of a HIFU transducer 90 generally similar to HIFU transducer 60' as described above in connection with FIGS. 7a and 7b, but configured to also angularly direct the ultrasonic energy generated by ultrasonic emitter 92 in the azimuthal plane. This, transducer 90 exhibits beam direction in both the elevational plane and the azimuthal plane. Due to the curvature of ultrasonic lens 94 along the azimuthal direction in the azimuthal plane, the beam is deflected outwards by an angle $\Theta$, as well as propagating forward. Such a configuration is particularly desirable, for example, in a tissue ablation device including a plurality of HIFU transducers 90 placed end-to-end along the azimuthal direction. One typically uses such a stringed device to create a substantially continuous lesion, for example an ablation lesion intended to isolate all or part of one or more pulmonary veins, such as disclosed in U.S. Pat. No. 6,805,128 to Pless et al. One of ordinary skill in the art will be familiar with the construction and function of such a tissue ablation device. By spreading the ultrasonic energy in the azimuthal direction, any potential gaps between HIFU transducers 90 can be targeted with ultrasonic energy (that is, adjacent ones of the plurality of HIFU transducer 90 ablation elements will have overlapping beams), thereby further facilitating creation of a substantially continuous lesion without the need to move the ablation device. The particular curvature of ultrasonic lens 94 may be adjusted such that the tissue in which the lesion is formed receives a generally uniform amount of ultrasonic energy.

FIG. 12 illustrates a HIFU transducer 100 incorporating an ultrasonic emitter 102 and an ultrasonic lens 104 integrated into housing 36. An intermediate compliance layer 106 is disposed between ultrasonic emitter 102 and ultrasonic lens 104. Compliance layer 106 is a stress mitigation feature, and is typically a material that flows or easily deforms in response to stress, such as a gel or Indium metal. Such a compliance layer can also serve as an acoustic matching layer and/or a thermal sinking layer. Note that the purpose of a compliance layer is to allow some local stress-relieving strain (compliance) to take place, whereas the stress-buffering layer described above prevents strain from taking place. In either case, however, the purpose of beneficially mitigating thermal mismatch stresses is served.

To manufacture a HIFU transducer according to the present invention, at least one ultrasonic emitter having a surface capable of emitting high intensity ultrasonic energy along a beam path and at least one low attenuation polymeric ultrasonic lens configured to direct or redirect ultrasonic energy passing therethrough are provided. The at least one ultrasonic emitter and the at least one polymeric ultrasonic lens are then acoustically coupled, for example by laminating or otherwise bonding the lenses to the emitters, such that the at least one polymeric ultrasonic lens can direct or redirect the high intensity ultrasonic energy emitted by the at least one ultrasonic emitter in at least one direction without succumbing to thermal degradation or thermal compromise. One or more stress mitigation features or thermal conduction features, such as the stress-buffering layers, matching layers, thermal-sinking layers, compliance layers, kerfs, and heat sinks described at length above, may also be introduced. Of course, any layer may be arranged so as to also act as an acoustic matching layer or electrode.

As described above, the ultrasonic emitter is preferably substantially flat as manufactured, preferably on both major faces, but at least on one major face. This permits ultrasonic emitters to be batch-manufactured as a slab that can thereafter be cut to form between about 10 and about 20 individual emitters at a time. Any acoustic matching layer, which is also preferably substantially flat, can be similarly batch-processed. A plurality of ultrasonic lenses may similarly be batch molded, cast, or thermoformed. By utilizing batch processing, one is not required to handle large numbers of relatively small parts until just before or at transducer lamination, providing a substantial manufacturing advantage. Furthermore, if the transducers are laminated at low temperatures or using ultraviolet-curing adhesives, several connected transducers may be batch processed for simultaneous lamination and divided thereafter. That is, a slab of ultrasonic emitters may be bonded to a slab of acoustic matching layer and a slab of ultrasonic lenses, and then the slab may be separated to form a plurality of HIFU transducers, which may then be assembled into a medical device such as a tissue ablation device.

It is also contemplated that, in addition to the lens, molding or casting manufacturing technologies may be applied to acoustic matching layers, stress-buffering layers, thermal-sinking layers, or compliance layers.

HIFU energy delivered by one or more HIFU transducers according to the present invention may be used to ablate tissue, for example in the treatment of cardiac arrhythmia. Thus, at least one ultrasonic emitter may be excited to generate high intensity ultrasonic energy along a beam path. The energy so generated may be directed (e.g., focused, collimated, or defocused) in at least one direction via at least one low attenuation polymeric ultrasonic lens positioned in the beam path and acoustically coupled to the ultrasonic emitter. The directed high intensity ultrasonic energy is then delivered to the tissue to be ablated, either to a single focus or to a plurality of foci, which may be on, beneath, or behind the tissue surface adjacent the HIFU transducer. During the ablation procedure, the operating temperature of one or more of the ultrasonic emitters and the ultrasonic lenses may be directly or indirectly monitored and regulated to remain below a thermal damage point, for example by flowing an ultrasonic transmission medium through the transducer to provide cooling thereto. The HIFU transducer(s) may be designed to have one or more localized or extended focal regions at one or more transducer operating conditions. The transducers may even be arranged to deliver thermally-conductive heating and lesioning to surface tissues at locations of weak acoustic focus.

An ablation device incorporating HIFU transducers according to the present invention, such as a belt- or wand-type ablation device for use on cardiac tissue, preferably delivers ultrasonic energy focused in at least one plane or to at least one point. Most commonly, in order to form an extended lesion, the transducers will focus the acoustic energy along an azimuthal direction. In particular, the ablation device preferably delivers focused ultrasound having a focal depth of about 2 mm to about 20 mm, more preferably of about 2 mm to about 12 mm, and most preferably of about 8 mm. Stated another way, a focus is spaced apart from the interface of the HIFU transducer and the tissue being treated along a focal axis (FA) within the stated ranges. The focused ultrasound also forms an angle of about 10 degrees to about 170 degrees, more preferably of about 30 degrees to about 90 degrees, and most preferably of about 60 degrees relative to the FA. Each HIFU transducer preferably has a length of about 0.43 inch, a width of about 0.35 inch, and a thickness of about 0.017 inch.

It should be understood that a transducer may be arranged to focus at one depth or at multiple depths over a focal range. Further, by varying frequency, the user can vary how much energy attenuates before reaching the focus. For example, a higher frequency will attenuate faster over depth than a lower frequency. This effect can be leveraged in a multi-step ablation algorithm, such as described below. Further, foci can also be mechanically moved by moving the transducer relative to the tissue, for example as by changing the inflated dimension of a saline-filled standoff or membrane. In addition, a multi-segment lens can be arranged, if desired, to have subsets of its lens segments focused at different depths, operating at the same or different frequencies.

An advantage of using focused ultrasonic energy for tissue ablation is that the energy can be concentrated within the tissue at depth. Another advantage of using focused ultrasound is that the directed energy diverges and reduces intensity after traveling beyond the focus, thereby reducing the possibility of damaging tissue beyond the target tissue depth as compared to more collimated ultrasonic energy. When ablating epicardial tissue with collimated ultrasound, the collimated ultrasound energy, if not strongly attenuated, is not absorbed by the immediately adjacent target tissue and travels through the heart chamber and remains concentrated on a relatively small area when it reaches the endocardial surface on the other side of the chamber. The present invention reduces the likelihood of damage to other structures since the ultrasonic energy diverges beyond the focus and is spread over a larger area at any downstream impact point. As touched on above in the discussion of FIGS. 11a and 11b, the ultrasonic energy may be produced by a number of HIFU transducers oriented to focus or concentrate ultrasonic energy, such as at least about 90% of the energy, within preferred angle ranges and radii of curvature. In another aspect of the invention, the transducers may be operated during two different time periods while varying at least one characteristic, such as the frequency of the ablating energy, the power of the ablating energy, the position of the focus relative to the tissue, and/or the ablating time. For example, HIFU transducers may be operated at varying frequencies over time to ablate tissue in a controlled manner. Specifically, the HIFU transducers are preferably operated to create a transmural lesion by controlling the delivery of energy to the tissue. Although it is preferred to vary the frequency when ablating the tissue, the HIFU transducers may, of course, be operated at a single frequency without departing from the spirit and scope of the invention.

In a first treatment method of the present invention, the transducer is activated at a frequency of about 2 MHz to about 7 MHz, and preferably of about 3.5 MHz, and a power of about 80 watts to about 150 watts, and preferably of about 130 watts, in short bursts. For example, the transducer may be activated for about 0.01 second to about 2.0 seconds, and preferably for about 1.2 seconds. The transducer is inactive for about 2 seconds to about 90 seconds, more preferably about 5 seconds to about 80 seconds, and most preferably about 45 seconds between activations. In this manner, a controlled amount of accumulated energy can be delivered to the tissue in short bursts to heat tissue at and near the focus while minimizing the impact of blood cooling at the endocardium. Ablation at this frequency may continue until a controlled amount of energy is delivered, such as about 0.5 kilojoule to about 3 kilojoules. Treatment at this frequency in relatively short bursts produces localized heating at the focus. At the first frequency, energy is not absorbed as quickly in the tissue as it is at higher frequencies, so that heating at the focus is not significantly affected by absorption of ultrasound energy in tissue before reaching the focus.

Typically, in order to lesion the endocardium against and despite the cooling blood of the blood pool, one will deliver an adiabatic or near-adiabatic heating pulse as close to the tissue/blood interface as possible. Preferably, the heating pulse will be delivered slightly inside the tissue adjacent the blood pool. "Adiabatic" means that the acoustic attenuation heating is delivered faster than it has a chance to appreciably conduct away from its focal target. Typical adiabatic delivery involves short pulses, frequently on the order of a second, a fraction of a second, or even measured in milliseconds, which times are shorter than a thermal relaxation time of the target tissue. One may also beneficially precede this pulse with a non-adiabatic preheating to increase the target tissue several degrees, such that the adiabatic pulse has less overall heating to do. Typically, the acoustic power density at the focus will be between about 1000 W/cm$^2$ and about 5000 W/cm$^2$.

Following treatment at the first frequency, the transducer is operated for longer periods of time, preferably about 1 second to about 4 seconds, and more preferably about 2 seconds, to ablate tissue intermediately between the focus and the transducer. The frequency during this treatment is also preferably about 2 MHz to about 14 MHz, more preferably about 3 MHz to about 7 MHz, and most preferably about 6 MHz. The transducer is operated for about 0.7 second to about 4 seconds at a power of about 20 watts to about 80 watts, and preferably about 60 watts. The transducer is inactive for between about 3 seconds and about 60 seconds, and preferably for about 40 seconds, between each activation. In this manner, a controlled amount of energy can be delivered to heat tissue intermediately between the focus and the transducer. The treatment at this frequency may continue until a controlled amount of total energy is delivered, such as about 750 joules.

As a final treatment stage, the ultrasonic transducer is activated at a higher frequency to heat and ablate the near surface. The transducer is preferably operated at a frequency of between about 3 MHz and about 16 MHz, and preferably at about 6 MHz. The transducer is operated at lower power than the treatment methods above since the ultrasonic energy is rapidly absorbed by the tissue at these frequencies, so that the near surface is heated quickly. In a preferred method, the transducer is operated at about 2 watts to about 20 watts, and more preferably about 15 watts. The transducer is preferably operated for a sufficient duration to ablate tissue, such as about 20 seconds to about 80 seconds, and preferably about 40 seconds. Often, the near surface temperature will reach about 70 degrees C. to about 85 degrees C.

Each of the treatments described above may be used by itself or in combination with other treatments. Furthermore, the combination of transducer size, power, frequency, activation time, and focal length may all be varied to produce the desired delivery of ultrasound energy to the tissue. As such, it is understood that the preferred embodiment may be adjusted by adjusting one or more of the characteristics and, thus, these parameters may be changed without departing from the spirit and scope of the invention. The treatment sequence described above generally delivers energy closer to the near surface during the second treatment and even closer to the near surface for the third treatment (that is, it ablates tissue from the far surface towards the near surface in successive treatments).

The focus of the ultrasound energy may also be moved relative to the tissue to deliver energy to different depths in the tissue. The HIFU transducer can be moved closer to and farther away from the target tissue, for example via variable membrane water-inflation, for example, with membrane 34 conforming to the required shape to fill the gap between the transducer and the tissue. Membrane 34 is preferably inflated, for example utilizing a pressurized fluid such as saline, and deflated to mechanically move the focus in this manner. However, the transducer may also be moved with any other suitable mechanism, such as lifting it from the tissue via a threaded foot, preferably located outside the beam. The focus may be moved or scanned while the transducers are activated or may be moved between activations of the transducers. Moving the focus of the ultrasound energy may be sufficient to create a transmural lesion without changing frequencies, or may be used in conjunction with a change in frequencies as described above. The focus may also be moved in any other manner such as with a phased array or variable acoustic lensing, such as a palette of interchangeable ultrasonic lenses from which the physician can choose before, or even during, the procedure.

Although several embodiments of this invention have been described above with a certain degree of particularity, those skilled in the art could make numerous alterations to the disclosed embodiments without departing from the spirit or scope of this invention. For example, one skilled in the art will appreciate that the labels used herein to describe the surfaces of first ultrasonic emitter 12 are merely a matter of convenience and could be reversed or altered without departing from the spirit and scope of the present invention (that is, it is within the spirit and scope of the present invention for ultrasonic energy to emanate from second surface 18 instead of, or in addition to, first surface 16).

Further, though all transducers described herein were generally rectangular in shape, the present invention is applicable to transducers of any shape, including rotationally symmetric transducers.

In addition, though the present invention has been described in the context of HIFU transducers utilized to provide ablation therapy to a patient, it is within the spirit and scope of the invention to apply the principles disclosed herein to other applications, such as metrology and imaging.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of ablating tissue, comprising:
exciting at least one ultrasonic emitter to generate high intensity ultrasonic energy along a beam path, the high intensity ultrasonic energy having an instantaneous power density of at least 1000 W/cm2 at one or more locations within the beam path;
directing the high intensity ultrasonic energy in at least one direction with at least one polymeric ultrasonic lens positioned in the beam path and acoustically coupled to the at least one ultrasonic emitter, the at least one polymeric ultrasonic lens having an attenuation at or less than 2 dB/cm-MHz when measured at room temperature; and
delivering the directed high intensity ultrasonic energy to tissue to be ablated while using at least one stress mitigation feature to mitigate thermal expansion mismatch stresses arising between the at least one ultrasonic emitter and the at least one polymeric ultrasonic lens.

2. The method according to claim 1, wherein the step of directing the high intensity ultrasonic energy in at least one direction with at least one low attenuation polymeric ultrasonic lens positioned in the beam path comprises focusing the high intensity ultrasonic energy to at least one focus with at least one low attenuation polymeric ultrasonic lens.

3. The method according to claim 1, further comprising:
monitoring an operating temperature of one or more of the at least one ultrasonic emitter and the at least one ultrasonic lens; and
regulating the operating temperature to remain below a thermal damage point.

4. The method according to claim 1, wherein the at least one stress mitigation feature is selected from the group consisting of acoustic matching layers, heat sink features, kerfs, and any combinations thereof.

5. A high intensity focused ultrasound tissue ablation device, comprising a plurality of transducers, at least some of said plurality of transducers comprising:
at least one ultrasonic emitter having a substantially flat first surface, wherein said at least one ultrasonic emitter generates ultrasonic energy that propagates along a beam path from said first surface, the ultrasonic energy having a power density of at least 1000 W/cm2 at one or more locations within the beam path; and
at least one ultrasonic lens acoustically coupled to said first surface in the beam path of the ultrasonic energy propagating therefrom, such that said at least one ultrasonic lens can direct the ultrasonic energy propagating from the first ultrasonic emitter in at least one direction in order to deliver it to tissue to be ablated; and
at least one acoustic matching layer disposed between said at least one ultrasonic emitter and said at least one ultrasonic lens, wherein said at least one ultrasonic emitter and said at least one ultrasonic lens are acoustically coupled across said at least one acoustic matching layer,
wherein an attenuation of the at least one ultrasonic lens is low enough to prevent thermal damage to the at least one ultrasonic lens during operation of the tissue ablation device.

6. The device according to claim 5, further comprising at least one kerf in at least one of said at least one ultrasonic emitter and said at least one ultrasonic lens, wherein said at least one kerf acts to mitigate thermal expansion mismatch stresses arising between said at least one ultrasonic emitter and said at least one ultrasonic lens during operation of said plurality of transducers.

7. The device according to claim 5, further comprising at least one heat sink, wherein said at least one heat sink acts to mitigate at least one of a thermal gradient and a peak temperature in said plurality of transducers.

8. The device according to claim 5, wherein said at least one acoustic matching layer acts to mitigate thermal expansion mismatch stresses arising between said at least one ultrasonic emitter and said at least one ultrasonic lens during operation of said plurality of transducers.

9. The device according to claim 5, wherein said at least one ultrasonic lens spreads said high intensity ultrasonic energy in at least one direction such that energy emitted by adjacent ones of said plurality of transducers overlaps.

10. The device according to claim 5, wherein said plurality of transducers are arranged to wrap about a least a portion of a pulmonary vein.

11. The device according to claim 5, wherein said high intensity ultrasonic energy has a frequency between 2 MHz to 7 MHz and a power between 80 W to 150 W.

12. The device according to claim 11, wherein the frequency is 3.5 MHz and the power is 130 W.

13. The device according to claim 5, wherein said high intensity ultrasonic energy has a frequency between 2 MHz to 14 MHz and a power between 20 W to 80 W.

14. The device according to claim 13, wherein the frequency is 6 MHz and the power is 60 W.

15. The device according to claim 5, wherein said high intensity ultrasonic energy has a frequency between 3 MHz to 16 MHz and a power between 2 W to 20 W.

16. The device according to claim 15, wherein the frequency is 6 MHz and the power is about 15 W.

17. The device according to claim 5, wherein at least some of the plurality of transducers further comprise a conformal acoustically transmissive membrane disposed over at least a portion of the beam path, wherein the conformal acoustically transmissive membrane at least partially defines a chamber for a flowable ultrasonic transmission medium.

18. A high intensity focused ultrasound tissue ablation device, comprising a plurality of transducers, at least some of said plurality of transducers comprising:
at least one ultrasonic emitter having a monotonically curvilinear first surface, wherein said at least one ultrasonic emitter generates ultrasonic energy that propagates along a beam path from said first surface, the ultrasonic energy having a power density of at least 1000 W/cm2 at one or more locations within the beam path; and
at least one ultrasonic lens acoustically coupled to said first surface in the beam path of the ultrasonic energy propagating therefrom, such that said at least one ultrasonic lens can direct the ultrasonic energy propagating from the first ultrasonic emitter in at least one direction in order to deliver it to tissue to be ablated,
wherein an attenuation of the at least one ultrasonic lens is low enough to prevent thermal damage to the at least one ultrasonic lens during operation of the tissue ablation device.

19. The device according to claim 18, wherein at least some of the plurality of transducers further comprise a conformal acoustically transmissive membrane disposed over at least a portion of the beam path, wherein the conformal acoustically transmissive membrane at least partially defines a chamber for a flowable ultrasonic transmission medium.

* * * * *